United States Patent
Dobler et al.

(10) Patent No.: US 6,358,474 B1
(45) Date of Patent: Mar. 19, 2002

(54) DEVICE AND METHOD FOR ISOLATING CELL MATERIAL OUT OF A TISSUE MEDIUM AND/OR A LIQUID

(75) Inventors: Hannes Dobler, Rutesheim; Claus Kuhn, Dürnau; Hans Lindner, Stuttgart; Stefan Kiesewetter, Ostfildern; Jürgen Bernhagen, Tübingen; Gabriele Tolle, Ludwigsburg; Günter Tovar, Stuttgart, all of (DE)

(73) Assignee: Fraunhofer Gesellschaft zur Förderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 09/462,409
(22) PCT Filed: Mar. 24, 1998
(86) PCT No.: PCT/DE98/00864
§ 371 Date: Apr. 26, 2000
§ 102(e) Date: Apr. 26, 2000
(87) PCT Pub. No.: WO99/02958
PCT Pub. Date: Jan. 21, 1999

(30) Foreign Application Priority Data

Jul. 8, 1997 (DE) ......................................... 197 29 028

(51) Int. Cl.[7] ................................................ C12M 1/00
(52) U.S. Cl. ................... 422/99; 435/283.1; 435/297.1; 435/267; 435/270; 435/286.4; 210/236; 210/87; 210/669; 215/247
(58) Field of Search ................. 435/286, 311, 435/270, 1.3, 267, 297.1; 210/87, 236, 669; 422/99

(56) References Cited

U.S. PATENT DOCUMENTS

| | | | |
|---|---|---|---|
| 3,709,395 A | * 1/1973 | Brennan et al. | |
| 3,941,317 A | 3/1976 | Kanor | ........................ 241/21 |
| 4,065,383 A | * 12/1977 | Skare et al. | |
| 4,317,726 A | * 3/1982 | Shepel | |
| 4,350,768 A | 9/1982 | Tibon et al. | ................ 435/241 |
| 4,413,059 A | * 11/1983 | Tihon et al. | |
| 5,114,858 A | * 5/1992 | Williams et al. | |
| 5,330,916 A | * 7/1994 | Williams et al. | |
| 5,372,945 A | * 12/1994 | Alchas et al. | |
| 5,376,263 A | * 12/1994 | Fischel | |
| 5,391,496 A | * 2/1995 | Kayal et al. | |
| 6,120,985 A | * 9/2000 | Laugharn, Jr. et al. | |

FOREIGN PATENT DOCUMENTS

| | | |
|---|---|---|
| EP | 0 590 504 | 4/1994 |
| GB | 2 100 137 | 12/1982 |

* cited by examiner

Primary Examiner—Jill Warden
Assistant Examiner—Brian Sines
(74) Attorney, Agent, or Firm—Crowell & Moring LLP

(57) ABSTRACT

An apparatus for isolating cell material from a tissue system and/or a liquid includes (1) a vessel open at the top, into which the cell material to be isolated can be introduced in the tissue system and/or the liquid; and (2) a separating device having a stamp-shaped configuration and including a flat separating disk having a peripheral edge fitting with the inner walls of the vessel in a fluid-tight manner and presenting at least one passage opening which is covered by a filter membrane, and which device can be inserted from the top into the vessel. The isolating disk pressurises the cell material inclusive of the tissue system and/or the liquid and acts thereupon with shearing forces by rotation. The cells and/or cell systems pass through the pores of the filter membrane whereas the residual tissue material is retained.

16 Claims, 2 Drawing Sheets

DEVICE AND METHOD FOR ISOLATING CELL MATERIAL OUT OF A TISSUE MEDIUM AND/OR A LIQUID

FIELD OF THE INVENTION

The present invention relates to an apparatus for as well as to a method of isolating cell material from a tissue system and/or a liquid.

PRIOR ART

Individual cells or cell systems are analysed for the medical diagnosis of clinical conditions and for scientific research applications, particularly in the field of bioengineering. The prerequisite for the analytical methods to be performed on cells is the isolation of individual cells from tissue systems or from liquids, respectively, where the individual cells occur in their natural form. In many cases, cells are sampled for the cell analysis from biological soft tissue such as from the spleen, the liver, and also from harder tissue such as the skin or hair. As part of the analysis of blood or urine, cells are frequently isolated from liquids, which are then analysed, for instance, to detect pathogenic agents. Such analyses also cover cells contained in body secretions, smears or other endogenous liquids, which cells, however, must be isolated from the individual tissue systems or liquids like in all the other aforementioned cases.

So far, however, standardised cell isolation methods have not become known. Predominantly, the manual separation of individual cells or cell agglomerates from tissue systems and/or liquids has been employed so far so that various, individually developed manual methods are applied for extracting cells from tissue, e. g. the spleen, which are adapted to the skill of the respective analysing operator. In this manner, different cell-isolating techniques have been devised in the course of time, which went then through different developments. Moreover, any helpful hints cannot be derived from the pertinent literature from which generally common or even standardised methods of universal cell isolation could be derived.

The production of a single-cell suspension for the analysis of a specific cell type require a number of operating steps to be performed in succession, which have been performed by hand exclusively to date.

For the analysis of cells occurring in tissue systems first of all a piece of tissue, e. g. from the spleen or the liver, must be severed in the desired size. The removed tissue sample is usually placed into a medium which is introduced, together with the sample, into a flat laboratory dish. Subsequently, the tissue sample contained in the medium is mechanically crushed and comminuted by means of suitable tools so that the cells to be analysed can be better extracted from the tissue. The cells or cell agglomerates, which are concentrated in the medium and are isolated from the individual crushed tissue particles can now be removed as a suspension from the medium contained in the laboratory dish. Using a pipette whereof the opening can be easily clogged, however, by extracted minor tissue particles usually performs this separation. The pipetting of the cell suspension therefore requires the respective operator to apply a particular manual skill because the isolated cells are present in the medium together with the tissue particles comminuted by the operation of mechanical isolation.

The cell suspension obtained by pipetting is introduced into a vessel again where the minor tissue fragments, which are removed together with the cells, can settle on the bottom of the vessel by sedimentation processes due to their greater mass. The afore-described pipetting operation is repeated again in order to obtain in this manner a suspension enriched with the cells. Depending on the type, size and percentage of extracted small tissue fragments present in the suspension, the extracting operation, which is based on sedimentation, must be repeated rather frequently. This operation can also be assisted by the application of centrifuges.

For the dissolution and separation of cell systems present in the suspension into individual cells, the suspension enriched with cell material is extracted by pipetting several times so that as many cells as possible will be present in an isolated condition in the suspension. The suspension of individual isolated cells from the tissue system, which is obtained in this manner, is usually transferred into another vessel into which ammonium chloride is added, for instance, for removing the red blood cells which are equally present in the suspension.

The afore-described methodology of cell isolation, e.g. of cells from a tissue fragment, e. g. of the liver, has gone to show that a great number of isolating steps is required which must be performed by hand in succession until individual isolated cells can be obtained. With each of the individual isolating steps, however, residual waste is produced which is difficult to discharge, such as the suspension liquids, the tools required for the isolating process like pipetting tips or isolating apparatuses and also the vessels used.

In an approach' to cut the expenditure entailed by the isolating operation many laboratories such as diagnostic PCR laboratories desist from the specific production of isolated cell suspensions and rather digest the complete tissue system. Even though this involves savings in terms of time it results in the disadvantage that inhomogeneous homogenisation products with a plurality of cell types, tissue fragments and frequently inhibiting substances for the subsequent analysis are produced.

BRIEF DESCRIPTION OF THE INVENTION

The present invention is therefore based on the problem of providing an apparatus as well as a method of isolating cell material from a tissue system and/or a liquid in such a way that the number of the manual operating steps to be performed will be reduced and that the cell isolation operation will be largely standardised so as to be able to obtain a reliable reproducibility of the analysis results linked up with the cell isolation. The waste resulting from each separate isolation operation, such as the flat laboratory dish as well as general vessels and tools, should be moreover reduced. In particular, the contamination of the operating place, which inevitably occurs with the conventional method, should be largely avoided.

The solution to the problem is solved by the apparatus and method of isolating cell material from a tissue system and/or a liquid according to the present invention.

The invention is based on the idea of providing a sample carrier system, which integrates all the functions for cell isolation from a tissue as well as for accumulation of cells from a liquid.

In accordance with the invention, the apparatus for isolating cell material from a tissue system and/or a liquid comprises a vessel open at the top, into which the cell material to be isolated can be introduced in the tissue system and/or in the liquid. Moreover, an isolating device having a die-shaped configuration is provided which comprises a flat isolating disk having a peripheral edge which is fluid-tight and flush with the inside walls of the vessel and presents at least one passage opening covered by a filter membrane. The isolating device can be inserted into the vessel from the top so that the isolating disk pressurises the cell material inclusive of the tissue system and/or the liquid and subjects it, by rotation, to shearing forces. In this system the isolating disk is so designed—and preferably provided with grinding elements on its underside—so that the cell material will be comminuted inside the vessel as the isolating disk rotates.

The application of the inventive apparatus makes it possible that following the sampling operation, e. g. in a physician's office, the taken sample as well as reagents assisting the process, if this is possible, can be transferred into the inventive container for transport. With an appropriate dimensioning of the vessel it is possible, at the same time, to determine the size of the tissue sample to be taken so that in this manner markings to be applied appropriately on the vessel will signal to the physician which tissue volume is required for the respective analysis.

This provision equally satisfies the demand for standardisation in the performance of such tissue analyses.

When the tissue sample in the closable container has arrived in the analysis laboratory the appropriate reagents can be introduced into the vessel for the subsequent isolating operation in the laboratory. The isolating device, which presents a die-shaped configuration and which is inserted into the interior of the vessel from the top, is used for cell isolation. In accordance with the present invention, the isolating device is designed to have an isolating disk, which bears flush against the inner wall of the vessel and is adapted to be lowered into the vessel via an actuating shaft in a vertical downward direction. The isolating disk is so configured that it presents passage openings which are each additionally coated with a filter membrane. The filter membrane presents membrane pores which have a size corresponding to the respective cells or cell systems to be isolated. As the isolating device is lowered inside the vessel in a direction towards the tissue sample present in a solution, the solution as well as the cells or cell systems isolated from the tissue sample may pass through the filter membrane and arrive in the upper region of the vessel. In this way two space regions are created in the vessel which are separated from each other by the isolating disk. The piece of tissue, which is present in the solution, is below the isolating disk whereas the isolated cells or cell systems, which are present in a suspension, are above the isolating disk.

Grinding elements in the form of pointed or angular projections are preferably provided On the underside of the isolating disk, which so to speak tear up the tissue sample as the isolating disk is lowered and rotated so that the cells or cell systems present in the tissue sample will be present in the form of a suspension as completely as possible and thus can pass through the filter membrane into the upper part of the vessel.

The isolating disk can be lowered into the vessel and rotated in a controlled manner via the actuating shaft which is both mounted as central holding shaft on the isolating disk or configured as hollow cylinder flush with the peripheral edge of the isolating disk, so that compressing and shearing forces can be selectively exerted on the tissue sample present in the solution. With the assistance afforded by the grinding elements provided on the isolating disk it is possible to realise a highly efficient separation of the cells or cell systems to be isolated from the tissue sample.

Due to the spatial separation of the cells and cell systems present in suspended form from the comminuted tissue fragments present under the isolating disk, it is possible to remove, by means of usual pipettes, the cell suspension above the isolating disk from the vessel, without running the risk of small tissue fragments clogging the pipette opening. Subsequent to the appropriate removal of the cell suspension by pipetting or decanting the residual tissue materials and reagents present in the vessel below the isolating disk can be disposed of together with the vessel.

The inventive apparatus makes it hence possible to implement a sample carrier and cell isolation system which is suitable for both receiving the tissue samples and the transport into an analysis laboratory, as well as the entire isolating process and the final discharge, despite the high demands on sterility. With the specification of suitable volume sizes of the containers a better standardisation of tissue analyses can be achieved so that the analysis results can be obtained with a more reliable reproducibility.

Due to the isolating device of the inventive configuration it is firstly possible to increase the processing rate of the cell isolation operation substantially, and secondly to reduce the amount of manual work for performance of the cell isolation. With the entire isolating process taking place in one and the same vessel the risks of mutual contamination with other samples or persons or objects can be reduced to a minimum.

The actuating shaft which is provided for handling the isolating device can be expediently operated both manually or even in an automated form. In addition to the provision that the actuating shaft is detachably fixed to a closure cap closing the vessel and that in this way a simplified manual handling of the isolating device can be implemented, the actuating shaft may also be provided with a flange for automatic actuation by means of an appropriate handling device such as a robot arm. With the application of automatic movers it is possible to perform fully automatic cell isolation, using the inventive sample carrier system. This aspect, in its turn, approaches the aim of a standardised cell isolation method with the associated high degree of reproducibility more closely.

Also in view of the ever-increasing awareness of environmental problems, the inventive sample carrier system contributes to a minimisation of the waste products to be disposed of as only a single vessel is used.

BRIEF DESCRIPTION OF THE DRAWINGS

The invention will be described by the example of one embodiment with reference to the drawing wherein.

DETAILED DESCRIPTION OF THE DRAWINGS

Figure 1:
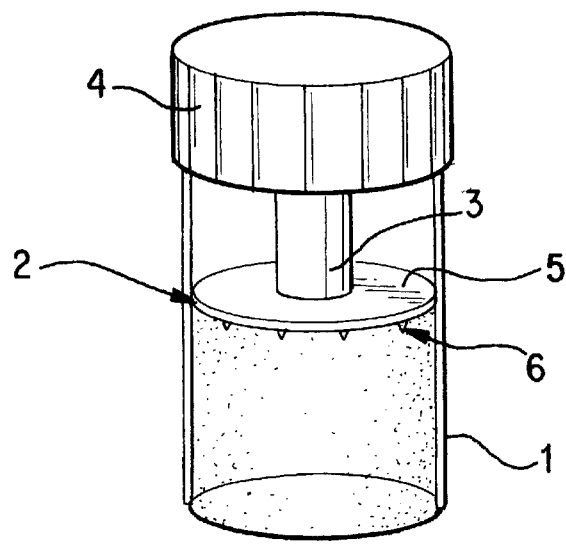
FIG. 1 is a view of the sample carrier system.
Figures 2A, 2B:
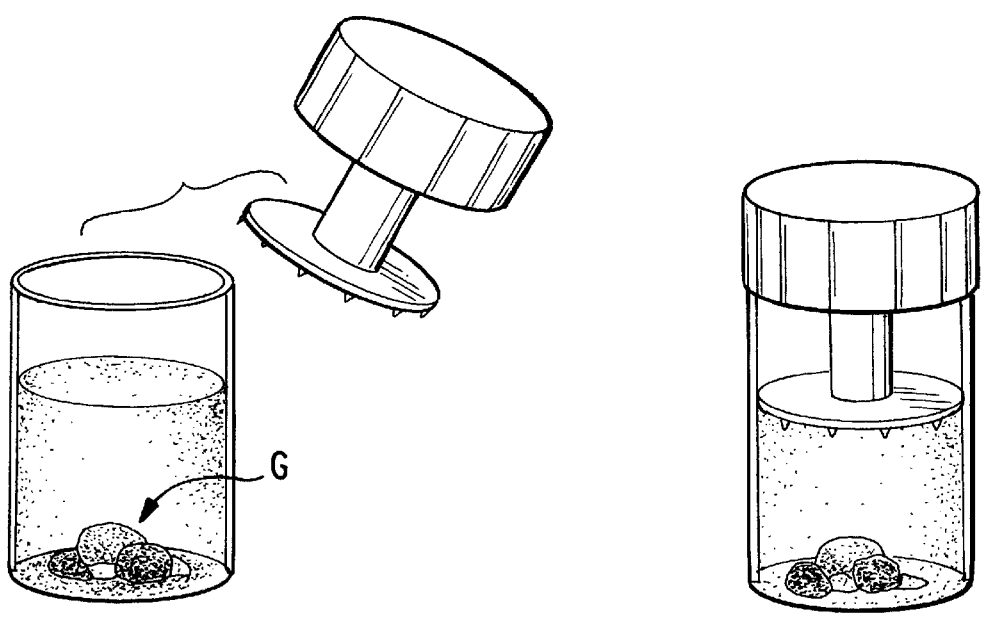
FIG. 2 shows the sequence of operations in the application of the sample carrier system.
Figure 2C:
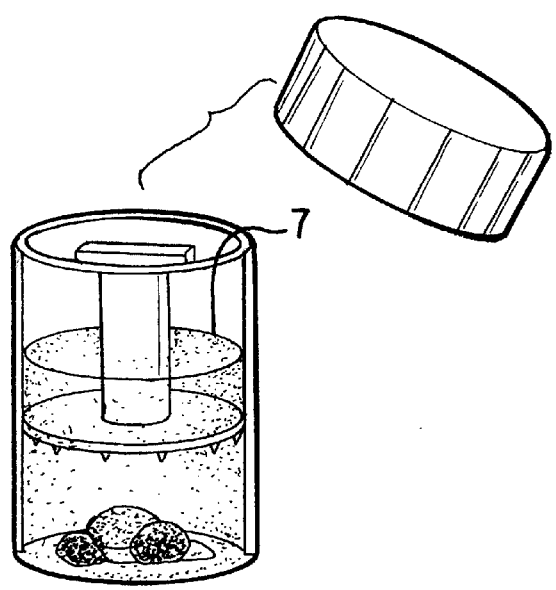
Figure 2D:
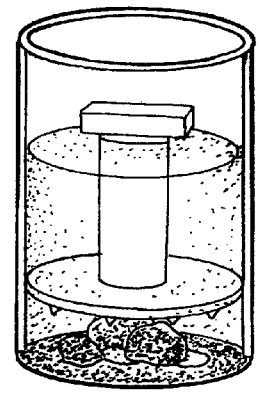
Figure 2E:
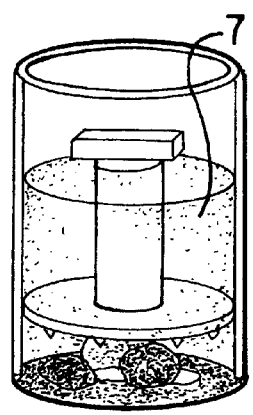
Figure 2F:
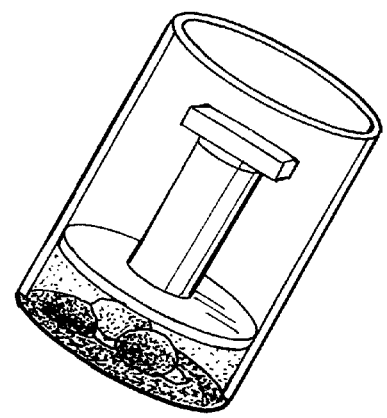

The inventive sample carrier system consists of a vessel 1 having a preferably cylindrical configuration, which has an upper opening in a way resembling a beaker. An isolating device consisting of an isolating disk 2 and an actuating shaft 3 can be introduced through the upper opening of the vessel 1, which in the embodiment illustrated here is closed by a screw-on lid 4. The actuating shaft 3 is centrally seated on the isolating disk 2 and is fixedly connected thereto. On the other side of the actuating shaft 2 the latter can be detachably fixed to the screw-on lid 4, which closes the vessel in a fluid-tight manner. The screw-on lid 4 presents a septum on its upper surface, which is suitable for piercing through pipetting needles for removal of the cell suspension.

By means of the actuating shaft 3 it is possible to transmit selective momenta on the isolating disk 2 by driving the actuating shaft 3 for rotation about its shaft axis and/or in a vertical direction. In particular, an adapter or a flange is mounted on the upper section of the actuating shaft 3 for automatic handler devices such as a robot arm (which are not illustrated in FIG. 1).

The isolating disk 2 has passage openings on its annular surface which are covered by a filter membrane 5. The pore size of the filter membrane depends on the respective original tissue and the cell size; for the analysis of liver cells it amounts to roughly 100 μm as a rule.

Grinding elements 6 are provided on the underside of the isolating disk 2, which, in the figure illustrated here, are formed as pointed edges. As the isolating device is appropriately lowered, the grinding elements 6 drill into the tissue fragment (not illustrated in FIG. 1) present below the isolating disk, and comminute the tissue material in such a way that the cells and cell agglomerates contained in the tissue can preferably be extracted therefrom.

The vessel illustrated in FIG. 1 is made of a synthetic material, which can be easily sterilised; for better visual observation of the isolating processes taking place inside the vessel the container is made to be transparent to light.

In an alternative to the geometry of the actuating shaft 3 as illustrated in FIG. 1, this shaft may be configured as hollow cylinder, which joins and is flush with the peripheral outer edge of the isolating disk 2. With such a configuration of the actuating shaft it is possible to make use of the entire area of the isolating disk 2 for the isolation process, which means that the area, too, which in the illustrated embodiment is covered by the centrally disposed actuating shaft on the isolating disk, produces a filter effect.

In the representation of process sequences according to FIG. 2 an expedient way of application of the inventive sample carrier system is shown. In the first sequence view tissue fragments G to be analysed are transferred into the interior of the vessel 1. Additionally, a liquid is introduced for dissolving the cells or cell systems contained in the tissue material, such as a saline solution and/or an ammonium chloride solution for removal of red blood cells.

In the second step, the tissue sample transferred into the vessel, inclusive of the solution, is closed by a closure cap in a fluid-tight manner and is now available for transport into from the analysis laboratory.

If necessary, further reagents may be supplied for improving the isolating reactions. To this end, either the closure cap must be removed from the vessel and the further reagents are then introduced into the interior of the vessel by means of a pipetting device 7 in accordance with the sequential view of the illustrated embodiment. In an alternative, the closure cap is provided with a septum, which may be pierced by means of appropriate pointed cannulae so as to introduce a liquid into the interior of the vessel whilst contamination with germs is avoided.

In the sequence view 4 the inventive isolating device is lowered in the vessel either by hand or in an automated system by means of a robot arm whilst it is caused to perform rotating movements at the same time so that the tissue fragments present on the bottom of the vessel are subjected to pressure and are comminuted under the action of shearing forces. With the outside periphery of the isolating disk 2 bearing against the inside of the vessel wall in a fluid-tight manner, the liquid present in the vessel as well as the cells or cell agglomerates extracted from the tissue material enter the upper region of the vessel exclusively through the filter membrane applied on the isolating disk.

In sequence 5 the cell suspension present above the isolating disk is removed by pipetting. There is, however, actually no risk of tissue fragments clogging the pipette opening because macroscopic tissue fragments cannot pass through the filter membrane.

Finally, by the end of the analysis according to sequence, nothing but the container together with the isolating device and the tissue material contained therein is left as residual waste.

LIST OF REFERENCE NUMERALS

| | |
|---|---|
| 1 | vessel |
| 2 | isolating disk |
| 3 | actuating shaft |
| 4 | screw-on lid |
| 5 | filter membrane |
| 6 | grinding elements |
| 7 | pipetting device |
| G | tissue fragments |

What is claimed is:

1. An apparatus for isolating cell material from at least one of a tissue system or a liquid, comprising:
   a vessel open at the top into which cell material in the tissue system or in the liquid can be introduced; and
   an isolating device comprising:
      an actuating shaft; and
      a flat isolating disk having grinding elements on an underside of the disk facing the bottom of said vessel; having a peripheral edge flush with inner walls of the vessel in a fluid-tight manner; and having at least one passage opening covered by a filter membrane, and which can be inserted into said vessel from the top;
      wherein said grinding elements introduce shearing forces into the cell material as said isolating disk rotates.

2. An apparatus according to claim 1, further comprising a closure cap that closes said vessel in a fluid-tight manner.

3. An apparatus according to claim 1, wherein said isolating disk pressurises said cell material.

4. An apparatus according to claim 1, wherein said isolating device comprises an actuating shaft centrally disposed on said isolating disk.

5. An apparatus according to claim 1, wherein said isolating device comprises an actuating shaft having the shape of a hollow cylinder which is flush with the peripheral edge.

6. An apparatus according to claim 5, wherein said isolating device is adapted to be driven via said actuating shaft for at least one of rotational or vertical movement.

7. An apparatus according to claim 5, wherein an upper end of said actuating shaft is adapted to be detachably fastened or fixedly mounted on said closure cap.

8. An apparatus according to claim 5, wherein said actuating shaft comprises a flange for automatic or manual actuation by a handling device.

9. An apparatus according to claim 2, wherein said closure cap is a screw-on cap.

10. An apparatus according to claim 2, wherein said closure cap comprises a septum for piercing by means of cannulae.

11. An apparatus according to claim 1, wherein said vessel is made of a synthetic material.

12. An apparatus according to claim 1, wherein said filter membrane comprises pores that ensure passage of individual cells or cell systems through the membrane and that retain remaining tissue material.

13. An apparatus according to claim 12, wherein said pores have a size of approximately 100 µm.

14. An apparatus according to claim 1, wherein said flat isolating disk has a plurality of openings that are covered by the filter membrane.

15. An apparatus according to claim 1, wherein said grinding elements are pointed edges.

16. An apparatus for isolating cell material from at least one of a tissue system or a liquid, consisting of:
   a vessel open at the top into which cell material in the tissue system or in the liquid can be introduced; and
   an isolating device comprising:
      an actuating shaft and
      a flat isolating disk having grinding elements and having a peripheral edge flush with inner walls of the vessel in a fluid-tight manner and having at least one passage opening covered by a filter membrane, and which can be inserted into said vessel from the top;
   wherein said grinding elements introduce shearing forces into the cell material as said isolating disk rotates.

* * * * *